United States Patent [19]

Cielo et al.

[11] Patent Number: 4,752,140
[45] Date of Patent: Jun. 21, 1988

[54] PULSED DILATOMETRIC METHOD AND DEVICE FOR THE DETECTION OF DELAMINATIONS

[75] Inventors: Paolo Cielo; Gerard Rousset, both of Montreal, Canada

[73] Assignee: Canadian Patents and Development Limited/Societe Canadienne des Brevets et d'Exploitation Limitee, Ottawa, Canada

[21] Appl. No.: 914,728

[22] Filed: Oct. 1, 1986

Related U.S. Application Data

[63] Continuation-in-part of Ser. No. 557,441, Dec. 2, 1983, abandoned.

[51] Int. Cl.[4] ............................................. G01N 25/16
[52] U.S. Cl. ...................................... 374/55; 356/358; 374/57
[58] Field of Search ...................... 374/43, 45, 55, 121, 374/57, 161; 356/357, 371, 376; 219/10.57; 356/358

[56] References Cited

U.S. PATENT DOCUMENTS

| | | | |
|---|---|---|---|
| 3,462,602 | 8/1969 | Apple | 374/5 |
| 3,978,713 | 9/1976 | Penny | 374/7 |
| 4,243,327 | 1/1981 | Frosch et al. | 374/43 X |
| 4,484,820 | 11/1984 | Rosencwaig | 374/6 |
| 4,513,384 | 4/1985 | Rosencwaig | 374/4 X |
| 4,521,118 | 6/1985 | Rosencwaig | 374/5 |

OTHER PUBLICATIONS

"Thermoelastic Inspection of Layered Materials: Dynamic Analysis" P. Cielo et al, Materials Evaluation-Aug. 1985.
"Optothermal NDE of Thermal-Barrier Coatings", P. Cielo et al presented at 1985 ASM Metals Congress--Toronto, Oct. 12-17, 1985.

Primary Examiner—Daniel M. Yasich
Attorney, Agent, or Firm—Foley & Lardner, Schwartz, Jeffery, Schwaab, Mack, Blumenthal & Evans

[57] ABSTRACT

A method for the detection of delaminated areas in coated materials or layered composites, which allows free-air operation and can be used to scan portions of bulky materials on the spot. This method which makes it possible to detect very small delaminated areas in a very short time (less than 1 millisecond), with a very high sensitivity and without creation of excessive thermal stress in the inspected material, basically comprises the steps of: focusing pulsed, thermal radiations onto the structure to be inspected to produce a vertical displacement of its coating by thermal expansion if a delaminated area is present at the coating-to-substrate interface, and detecting and measuring this vertical displacement if any, by interferometry, preferably laser-beam interferometry. An apparatus for carrying out this method is also disclosed.

19 Claims, 3 Drawing Sheets

PULSED DILATOMETRIC METHOD AND DEVICE FOR THE DETECTION OF DELAMINATIONS

CROSS-REFERENCE

The present application is a continuation-in-part of application Ser. No. 557,441 filed on Dec. 2, 1983, now abandoned.

BACKGROUND OF THE INVENTION (a) Field of the Invention

The present invention relates to a method for detecting delaminations in coated materials or layered composites generally referred to hereinafter as "layered structures", and to a device for carrying out said method.

(b) Brief Description of the Prior Art

The detection of delaminations and layer unbonds caused by adhesive bond failure at the coating-to-substrate interfaces of coated materials or layered composites such as Al-epoxy laminates or fiber-epoxy structures is an important industrial problem, especially in the construction and aeronautic industries. Indeed, such delaminations and layer unbonds may propagate quickly under certain circumstances and result in a local failure of the coating. In the aeronautic industry, delamination of the aluminum skin adhesively bonded to the honeycomb core of an aircraft wing structure may for example generate in a fast-growing unbonded area and eventually in a catastrophic failure if the delamination is not detected when its diameter is subcritical, typically in the range of 0.5" to 1".

To solve this industrial problem, several methods have been developed for proceeding to a non-destructive inspection of coatings and thereby detecting delaminations in a fast and reliable manner.

A known method consists in subjecting the layered structure to ultrasonic pulse-echo testing. This method which basically consists in measuring the difference in the resonance frequency of an unbonded layer excited by contact with an ultrasonic transducer, is interesting but rather unpractical because it requires a time-consuming, manual scanning and a very good coupling between the surface and transducer, which coupling generally requires the use of an immersion bath.

Another known method for the early detection of delaminations is based on the detection of an acoustic emission. A major problem with this method is the signal interpretation.

A further known method which is relatively recent and considered as a promising approach in this field, consists in taking holographic exposures of the surface of a coating layer before and after deformation of this layer produced by either vacuum, vibration or surface heating. The superposition of the two holograms shows interference fringes when the unbonded surface layer has lifted under the action of the thermally- or vibration-induced stress. Such an optical holography is interesting because it is a non-contact method which does not require scanning. However, such a method has found very little application up to now outside of research laboratories for the following reasons:

(1) Holography is very sensitive to ambient vibrations.

As the exposure time for the holographic plate is relatively long (of the order of 1 second), the inspected structure must therefore be kept on a vibration-insulated table during its exposure, and this exposure must be carried out in absolute darkness while avoiding excessive air currents such as produced by an air conditioning system.

(2) Holography can only detect surface lifts corresponding typically to a vertical displacement of some micrometers. This requires a substantial amount of heating (typically to 10° or 20° C. above ambient), which in turn produces thermal deformations throughout the whole structure, thereby making fringe interpretation difficult. This heating may also cause damage to the adhesive bond.

(3) Holography is relatively unreliable, since the surface lift appears sometimes right after heating, sometimes during cooling depending on the relative thermal expansion coefficients of the surface layer and of the substrate. Moreover layer buckling is only apparent when the unbonded layer is initially convex.

Other methods and devices, for the detection of delaminations have also been proposed, such as for example, the method and sonomicroscope developed by L. W. Kessler and D. Yuhas and marketed by Sonoscan. According to this method, ultrasonic energy is produced by a piezoelectric transducer and applied to a sample. The ultrasonic waves which are transmitted through the sample, produce "ripples" on the sample surface or on a coverlip placed over this surface. Detection of said ripples which are indicative of the internal microelastic structure of the sample, is made by a sensitive, high resolution scanning laser beam microphone the signals of which are processed to form an acousting micrograph display image on a T.V. monitor.

Another method is disclosed in U.S. Pat. No. 3,462,602 to W. R. Apple and basically consists in heating the surface of a layered structure to be inspected with a heat-lamp or a hot-air gun and observing the appearance of the hot spots on the top of the delaminated areas with an IR camera. This infrared method is interesting but prone to errors because of variations in the surface emissivity.

A more quantitative method is described in U.S. Pat. No. 4,468,136 to Murphy and in U.S. Pat. Nos. 4,513,384; 4,521,118 and 4,522,510 to Rosencwaig, and is based on the propagation of thermal waves within the material to be inspected. According to this method, a modulated electron or laser beam is scanned across the surface of a sample. During this scanning, the beam is absorbed by the sample and causes a periodic heating of its surface at the modulation frequency. This heating is the source of thermal waves that propagate from the heated regions and may be acoustically or optically detected. Any sub-surface defect having thermal characteristics different from its surroundings will of course affect these thermal waves and become visible thereto.

This approach is interesting but is has some intrinsic limitations. One of them is that the light of the modulated laser beam may be scattered by the surface toward the detector generating spurious optical noise. A much more important limitation is related to the slow propagation velocity of thermal waves. In order to analyze the state of the coating-to-substrate interface, the modulation period must be of the order of the thermal propagation time through the coating:

$$t_{th} \simeq 1/f_m \simeq l^2/\alpha$$

where $f_m$ is the laser modulation frequency, $\alpha$ is the thermal diffusivity and l is the coating thickness. For a ceramic coating with $l=1$ mm and $\alpha=1$ mm$^2$/second, $t_{th}$ is equal to about 1 second, which means an observation time of at least 10 second if the measurement is extended over a sufficiently large number of modulation periods. This is unacceptably long if a coated part has to be inspected point-by-point for unbond defects over its whole surface.

OBJECTS OF THE INVENTION

The object of the present invention is to provide a method and a device for the detection of delaminations, which avoid most of the drawbacks or limitations of the known methods and devices referred to hereinabove.

More particularly, the object of the invention is to provide a method and a device for the detection of delaminations which allows free-air operation and can be used to some portions of bulky materials in situ and without contact. In addition, the method and device according to the invention make it possible to detect very small delaminated areas in a very short time (less than 1 millisecond), with a very high sensitivity and without creation of excessive thermal stress in the inspected material.

SUMMARY OF THE INVENTION

The method according to the invention is similar to the holographic method mentioned hereinabove, in that it also uses a thermal dilatometric approach for detecting the presence of delaminations. However, it substantially and essentially differs from this known method in that it makes use of an optical interferometer, preferably a laser-beam interferometer instead of a holographic device to detect localized vertical displacement or lift-up of the coating produced by surface heating.

Optical interferometry is a standard method for measuring thermal expansion especially of bulk solids, and applications of such a technique to microscopic imaging have already been suggested (see, for example, U.S. Pat. No. 3,390,730 to A. A. S. Laurens, and H. K. Wickramasinghe et al, Electron. Lett. 18, 700 (1982). Optical interferometry is also a standard method for inspecting unpolished surfaces and commercial interferometers capable of carrying out such inspections at operating distances of several meters are available.

However, to the best of the inventors' personal knowledge, it has never been suggested up to now to apply such a particular method to the detection of delaminations in spite of the numerous advantages that may derive therefrom such as, for example, the high sensitivity of its measurement. The main reason that can explain this lack of application, is probably the fact that optical interferometry is not applicable as such to the inspection of a layered structure. Indeed, lifting-up of an unbonded layer independently of its concavity or convexity or of the value of its thermal expansion coefficient with respect to the one of its substrate, can only be obtained if (1) the time of thermal propagation across the layer is longer that the heating period and (2) a radial thermal gradient is produced across this layer.

In accordance with the present invention, it has been discovered that the above mentioned, essential conditions can be achieved when use is made of an interferometric method, if the heating source used for producing the required lifting-up of the unbonded layer is pulsed and focused near the center of the unbonded area.

The method according to the invention for the detection of delaminated areas by thermal dilatometry in a layered structure comprising a substrate covered by a coating, comprises the basic steps of:

subjecting each surface area of the structure to be tested to a thermal radiation consisting of a short pulse having a pulse duration smaller than the inertial response time of the layered structure and in the range of 0.001 to 1 millisecond, and wherein the thermal radiation is focused onto the surface of said structure to irradiate a surface area which is smaller than the delaminated areas to be detected; and detecting vertical displacements of the structure surface by interferometry to indicate delaminations by:

measuring a first vertical displacement of the structure surface during the application of the thermal radiation pulse as a measure of the thermal expansion of the structure due to the energy absorbed by the structure.

measuring a second vertical displacement of the structure surface during the mechanical response time of the structure following the termination of the thermal radiation pulse as a measure of the thermal deformation in the structure, and using the first measured vertical displacement to normalize the second measured vertical displacement to provide an indication of a delamination.

In accordance with a preferred embodiment of the invention, the first vertical displacement measurement is obtained by determining the difference between an interferometric reading taken before the radiation pulse and an interferometric reading taken immediately after the termination of the radiation pulse. The second vertical displacement measurement is obtained by determining the difference between an interferometric reading taken before the radiation pulse and an interferometric reading taken a predetermined period of time after the termination of the radiation pulse equivalent to the mechanical response time of the structure. Alternatively, this second measurement can be obtained by determining the difference between an interferometric reading taken immediately after the applied radiation pulse and an interferometric reading a predetermined period of time after the termination of the radiation pulse equivalent to the mechanical response time of the structure.

In accordance with the invention, the thermal radiation focused onto the material is selected so that its pulse duration ranges from 0.001 to 1 millisecond. This thermal radiation may be a laser-beam generated by an auxiliary laser gun or by the laser-beam interferometer used for the detection and measurement step.

The advantage of using short pulses in the order of 1 millisecond or less, is that it allows satisfactory operation and measurement even in the presence of strong ambient vibrations. If the unbonded coating lift up measurement is carried out by measuring the difference existing between the interferometric readings obtained before and after application of heating, that is before and after each pulse, the whole measurement will take 1 millisecond. This in practice is equivalent to filtering out all the ambient vibration noise except for a frequency band centered on 1 kHz.

Moreover, the use of very short pulses, shorter than the inertial response time of the unbonded layer, is interesting in that it allows time-separation of the linear thermal expansion that always occurs, even if the coating is well-bonded onto the material, from the coating bending that occurs only if a delamination is present.

Indeed, only bending is affected by the inertial response time of the coating, the linear expansion being almost simultaneous with the heating pulse. Thus, the inertial response tine is the time delay required for a delaminated area of the structure to lift up to its maximum value when subjected to a pulsed thermoelastic excitation, due to the inertial properties of the structure.

The rapidity of such a pulsed dilatometric method makes it much more appropriate to point-by-point scanning as compared to the modulated thermal-wave approach. This becomes strikingly clear if it is considered that a 100 mm × 100 mm (4"×4") part with a 1 mm-thick coating can be fully inspected with a 1 mm² spatial resolution in 10 seconds with a 1 millisecond-per-spot method according to the invention, while taking $10^5$ seconds, or 27 hours, with the 10 seconds-per-spot thermal-wave method mentioned above. Finally, no radiation from the heating laser is present while observing the signal after the heating pulse, so that no spurious optical noise may be generated.

BRIEF DESCRIPTION OF THE DRAWINGS

The invention, the theory from which it derives, and some of its advantages will be better understood upon reading of the following non-restrictive description given with reference to the accompanying drawings wherein.

DETAILED DESCRIPTION OF THE INVENTION

Figure 1:
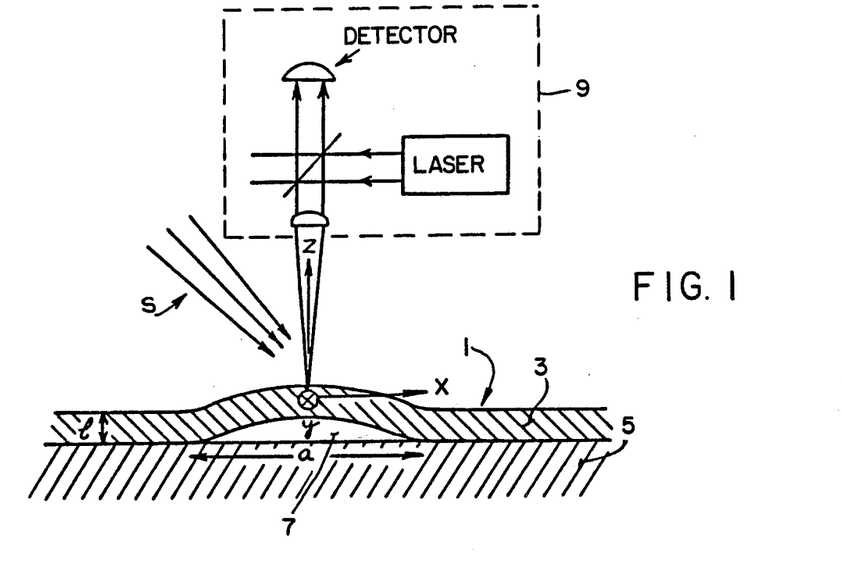
FIG. 1 is a schematic representation of a dilatometric device according to the invention, using a Michelson interferometer.

The device according to the invention as shown in FIG. 1, comprises a pulsed, thermal radiation source S, which may be a laser gun. The thermal radiations pulsed by the source S are focused onto the surface of a coated material 1 with a pulse duration lower than 1 millisecond to allow satisfactory operation even in the presence of strong ambient vibrations.

The source S is used to heat the surface of a layered structure 1 comprising a substrate 5 covered by a coating 3. The localized thermal gradients generated by the source S produce a bending force which in turn produces a lift-up of the coating 3 from its substrate 5 if a delaminated area 7 is present at the coating-to-substrate interface.

A theoretical, thermolelastic analysis of the thermal stress in the heated layer results in the following descriptive system of equations:

$$\frac{El^3}{12(1-\nu^2)} \nabla^4 w + \frac{E a_T}{1-\nu} \nabla^2 M_T = -\rho l \frac{\partial^2 w}{\partial t^2} + \quad (1)$$

$$\bar{\sigma}_{xx} \frac{\partial^2 w}{\partial x^2} + \bar{\sigma}_{yy} \frac{\partial^2 w}{\partial y^2} + 2\bar{\sigma}_{xy} \frac{\partial^2 w}{\partial x \partial y}$$

$$\frac{\partial \bar{\sigma}_{xx}}{\partial x} + \frac{\partial \bar{\sigma}_{xy}}{\partial y} = \rho l \frac{\partial^2 u}{\partial t^2} \quad (2)$$

-continued $$\frac{\partial \bar{\sigma}_{xy}}{\partial x} + \frac{\partial \bar{\sigma}_{yy}}{\partial y} = \rho l \frac{\partial^2 v}{\partial t^2} \quad (3)$$

where $\nabla^2 = \frac{\partial^2}{\partial x^2} + \frac{\partial^2}{\partial y^2}$;

$$\bar{\sigma}_{ij} = \int_{-\frac{l}{2}}^{\frac{l}{2}} \sigma_{ij} dz; \text{ and}$$

$$M_T = \int_{-\frac{l}{2}}^{\frac{l}{2}} Tz dz;$$

In all of these equations, E is Young's modulus, $\mu$ is the Poisson ratio, $a_T$ is the coefficient of linear thermal expansion, $\rho$ the density, l the thickness of the coating layer, $\sigma_{ij}$ are the stress components and u, v, w are the displacements in the x, y and z directions, respectively, the reference axes x, y and z being shown in FIG. 1. The boundary conditions correspond to $w = \partial w/\partial n = 0$; $u = 0$ and $v = 0$ on the edges of the unbonded area.

It is apparent that these coupled equations have a non-zero solution only if the term $\nabla^2 M_T$ is different from zero, i.e. if T=T (x,y,z). In other words, if T=T (x,y) (i.e., no thermal gradient across the thickness), or if T=T(z) (i.e., extended theral source), the initially flat layer will not move under heating.

The conclusion of this analysis is therefore that the heating source must be both pulsed and focused near the center of the unbonded region in order to produce the required lift-up of the unbonded layer. Indeed, if the diameter of the heating spot obtained by focusing the thermal radiation onto the structure is smaller than the diameter "a" of the delaminations to be detected, the thermal gradients generated at this spot will produce a bending force which in turn will produce a lifting force higher than the one that would be obtainable by volume-heating, especially at the beginning of the heating period. As a result, the initial lift-off of a thermally thick layer will be achieved.

Moreover, if the diameter of the heating spot is limited in length to heat, for example, an area of some mm² only, the whole-body bending problems that are encountered when relatively large surfaces of structure are heated, will be almost completely avoided. In this connection, it may be noted that such problems cannot be avoided when use is made of the above mentioned holographic method.

The device shown in FIG. 1 also comprises a laser-beam interferometer 9 for measuring the lift-up. This interferometer is of the well-known Michelson type.

As aforesaid, one of the main advantages of using an interferometer for detecting and measuring the vertical displacement of the coating is that very high sensitivities of, for example, 0.01 micrometers may be easily obtained. This makes it possible to detect delaminated areas much smaller than those detected by holography. This also permits to use a lower energy heating source and thereby to avoid potentially damaging, high thermal stresses in the inspected structure.

Another main advantage that derives from using an optical interferometer to measure the vertical displacement of the coating is that localized heating and dilatation probing can be performed point-by-point during a time that is much smaller than the ambient vibration period. Thanks to this very short time of measurement (less than 1 millisecond), the low-frequency ambient vibrations can be easily filtered out of the signal, thereby making the measurement possible without the need of a vibration-isolated table. Moreover, reduction in the measurement time causes a proportional reduction in the scanning time.

Figure 2:
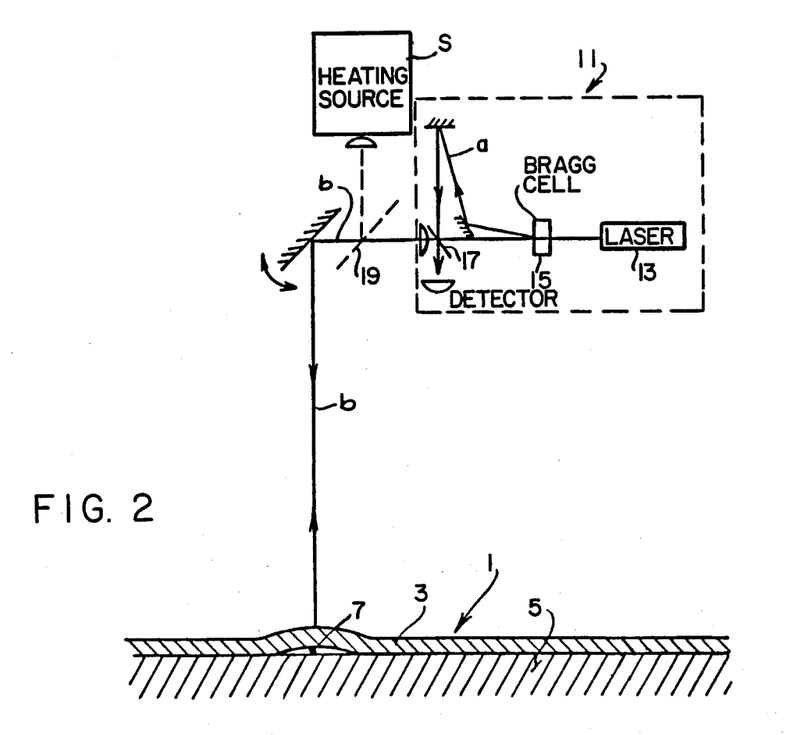
FIG. 2 is a schematic representation of another dilatometric device according to the invention, using a scannable laser-heterodyne interferometer.

The device according to the invention as shown in FIG. 2 comprises a laser-heterodyne interferometer 11. This interferometer comprises a laser gun 13 for producing a laser beam and a Bragg cell 15 for producing a frequency-shifted deflected beam (a) which is superposed to the main beam (b) reflected by a beam-splitter 17. The super-position of beams (a) and (b) gives a heterodyne beat signal at the difference between the frequencies of the two light beams. Vertical displacement of the surface of the layered structure 1 produces a Doppler shift which is detected as a variation of the beat frequency.

As heterodyne interferometer, use can be made, for example, of the interferometer marketed by the Danish company DISA/DANTEC. This interferometer has a sensitivity of 0.01 micrometers.

Of course, the surface of the structure has to be heated by pulsed thermal radiations focused thereon to perform the requested detection and measurement.

As shown in FIG. 2, these radiations may be supplied by an external laser beam source S. The beam of this source S is superposed to the beam of the interferometer by means of a dichroic mirror 19 which reflects the heating source wavelength and transmits the wavelength of the interferometer laser. An external mirror 21 can advantageously be made movable to allow easy scanning of the surface of the structure to be inspected.

Under certain circumstances, the laser beam generated by the interferometer may be used alone as heating source. In this case, the heating source S as well as the dichroic mirror 19 are omitted.

The signal which is detected by the device of either FIG. 1 or FIG. 2 when an unbonded coating layer is scanned, is composed of three components that are respectively associated to the following mechanisms:

(1) the layer lift-up caused by the thermal gradients in the unbonded layer;

(2) the thermal expansion of the heated structure, which increases the thickness of the layer; and (3) the variation in the refractive index of the air above the layer, which is conductively heated by contact with the heated surface.

Component No. 3 listed above depends on the thermal diffusivity of the layer. In practice, it is usually 10 times smaller than component No. 2.

As can be easily understood, only component No. 1 corresponds to the signal to be detected, components No. 2 and 3 being "noises" that are present whether the layer is bonded or unbonded. Only this component No. 1 is affected by the inertial mechanical response of the layer. Indeed, components No. 2 and 3 are practically simultaneous with the heating pulse.

Figure 3:
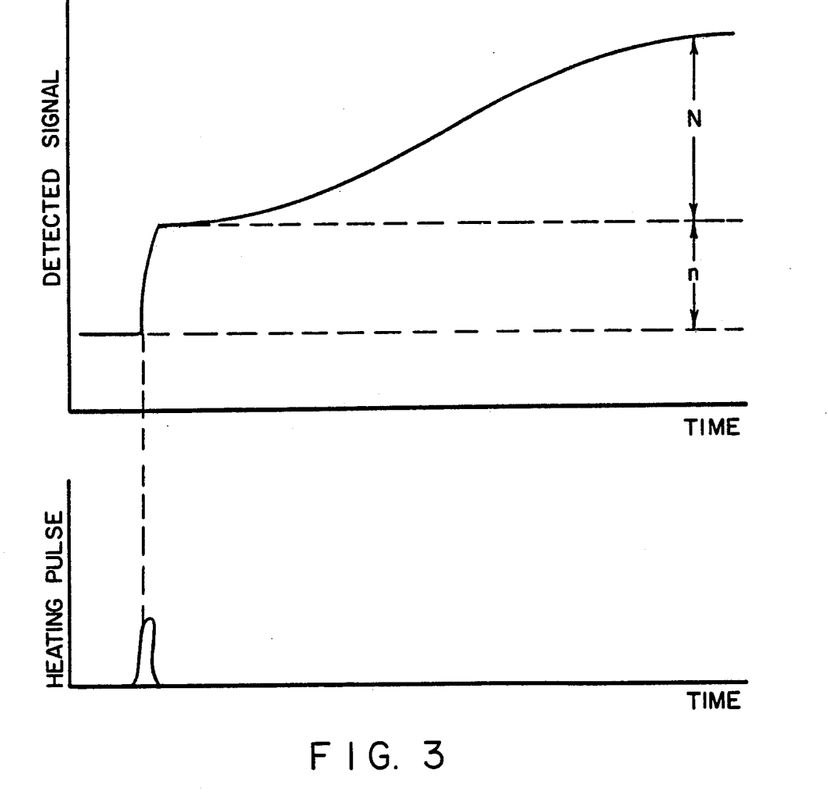
FIG. 3 are curves representative of a heating pulse and a detected signal as a function of the time.

Of course, this particular behaviour is used to differentiate between the signal component No. 1, and the noise components No. 2 and 3, as shown in FIG. 3.

As shown in this figure, the signal n detected right after a heating pulse is attributable to the above mentioned components No. 2 and 3 which are simultaneous with the pulse. The real signal N produced by the bending of the unbonded layer, takes place in a longer period, because it is subject to the inertial properties of the bending plate. Separate measurement of N and n permits to separate the real signal to be detected from the unwanted noise. Even more importantly, the measurement of n permits to estimate the absorbed power and thus to normalize the detected signal, thereby allowing a quantitative estimation of the delamination diameter "a". Indeed, the amount of absorbed heating power may vary depending on the absorptivity of the surface, which is often unpredictable with structures of industrial interest which cannot be carefully cleaned before inspection. The value of the signal n is proportional to the amount of absorbed power, so that the detected signal N can be normalized using this information.

More specifically, the normalization is performed by taking the ratio N/n of the signals specified in FIG. 3, and considering such a ratio as the output signal. Such a ratio is unaffected by variations in the source power, surface absorptivity or detector sensitivity, so that it provides a much more reliable parameter for the detection of delaminations.

The value of the normalized signal can be used to estimate the diameter "a" of the delamination. It can indeed be shown (see P. Cielo, Int. Adv. NDT, vol. 11, p. 175, 1985; Rousset et al., J. Appl. Phys., vol. 57, p. 4396, 1985; Cielo et al., Appl. Opt., Vol. 25, p. 1327, 1986) that the ratio N/n for a metallic coating on a metallic substrate is approximately equal to $(a/2)^2$, where is the known layer thickness as shown in FIG. 1. The minimum value of the delamination diameter which can be detected depends of the electronic noise of the interferometer detector, which has been found by the inventors to be of the order of magnitude of the thermal expansion amplitude n using standard components. Under such circumstances, the minimum delamination diameter which can be detected is of the order of twice the coating thickness.

Figure 4:
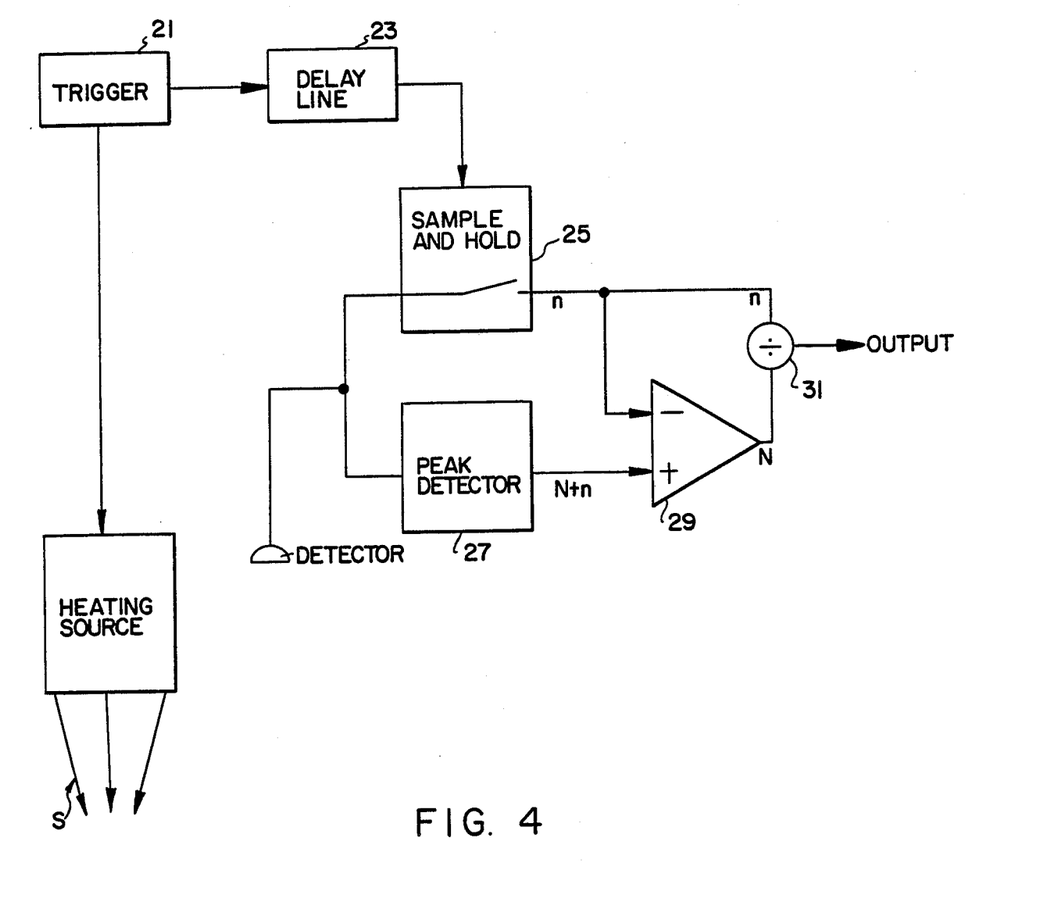
FIG. 4 is schematic representation of an electronic circuit for use in determining and treating the detected signals shown in FIG. 3.

The treatment of the signals detected with the device according to the invention in order to obtain a value of n, N and N/n can be carried out with an electronic circuit like the one schematically illustrated in FIG. 4. This circuit comprises a sample and hold circuit 25 and a peak detector 27 connected in parallel to the outlet of the detector of the laser interferometer 9 or 11. The circuit 25 is connected to, and controlled by the trigger 21 of the heating source S via a delay line 23 to allow measurement and holding of the signal n as soon as a heating pulse is triggered. The peak detector 27 which is also connected to the detector of the interferometer gives a signal equal to N+n. Subtraction from this signal of the signal n held in 25 through a subtractor 29 gives the signal N which is fed together with signal n to a divider 31 to give the requested normalized signal N/n as output.

As can now be clearly understood, the method according to the invention is based on the measurement of the transient displacement of an unbonded layer due to a transient surface thermal gradient produced in a radial direction by the absorbtion of a focused laser pulse.

In accordance with the invention, the measurement is carried out by subjecting each surface area of the structure to be tested, to a thermal radiation consisting of a short pulse generated by a laser, having a pulse duration smaller than the inertial response time of the layered structure, and detecting the vertical displacement of the structure surface by interferometry before and after absorption of each short pulse.

In order to be shorter than the mechanical response time of the layered structure, the laser pulse must have a duration shorter than 1 millisecond. If a longer observation time is required, i.e. if a focused, eventually modulated but not pulsed heat source is used, the interferometer would see a thermally induced displacement of the order of 1 micrometer in amplitude, superposed to ambient low-frequency surface vibrations which may reach amplitudes of hundreds of micrometers and be completely random. Thus, it would be impossible to separate the thermally induced displacement from the ambient vibrations in a noisy industrial environment.

In order to be efficient, the laser pulse must also be focused onto the surface of the structure to irradiate a surface area which is smaller than the delaminated area to be detected.

The method according to the invention makes use of a "pulsed" approach instead of using a "periodically modulated" approach as Murphy in his U.S. Pat. No. 4,468,136 and Rosencwaig in his U.S. Pat. Nos. 4,521,118 and 4,522,510. This "pulsed" approach which requires a measurement time of less than 1 millisecond, is unaffected by ambient vibrations of frequency lower than 1 kHz, while vibration noise of frequency higher than 1 kHz has an amplitude which is much smaller than the thermally induced displacement. The point-by-point scanning time for inspecting large surfaces is correspondingly reduced by several orders of magnitude.

Moreover, the detection of the thermally induced, vertical displacement is carried out by a "time-resolved" method which makes it possible to compare the surface displacement produced by linear expansion (i.e. the noise signal n in FIG. 3, which noise is proportional to the absorbed heat-pulse energy) to the surface displacement produced by the layer bending during the inertial response time of the structure to the thermal radiation pulse (i.e. the signal N in FIG. 3, which is also proportional to the absorbed heat-pulse energy). In addition, the measurement of the vertical displacement of the structure surface after the application of a thermal radiation pulse is obtained in a very accurate manner by first measuring the thermal expansion of the structure and subsequently using it to normalize the vertical displacement due to the presence of a delamination, thereby making it possible to obtain a quantitative estimation of the delamination diameter "a".

As aforesaid, the normalized ratio N/n is not affected by variations in the heating power or surface absorptivity, as the presence of an abnormally high surface absorbtivity can be easily detected from the level of the thermal-expansion signal n and can be "automatically" compensated by normaling the signal N with the signal n, i.e. taking the ratio N/n.

In this regard, the method and device according to the invention advantageously permits to avoid all the limitations of the holographic approach. In particular, the device according to the invention can be used in an industrial environment.

Although the method and device according to the invention have been described in use for the detection of coating delaminations, one can see that they can also be used for the detection of other kinds of structure defects such as those encountered in shallow-disbonded composite structures, or partially detached adhesive joints. In general they can be used to produce a map of the local thermal expansivity of any structure surface.

What is claimed is:

1. In a method for detecting delaminated areas by thermal dilatometry in a layered structure comprising a substrate covered by a coating, said method being of the type comprising the steps of:

subjecting each surface area of the structure to thermal radiation to produce a vertical displacement of its coating by thermal expansion wherever a delaminated area is present at the coating-to-substrate interface, and detecting and measuring this vertical displacement, if any, the improvements wherein:

the thermal radiation to which the structure is subjected, consists of a short pulse which has duration ranging from 0.001 to 1 millisecond and is smaller than the mechanical response time of the delaminated area;

said thermal radiation is focused onto the surface of said structure to irradiate a surface area which is smaller than the smallest delaminated area which is to be detected; and the vertical displacement of the coating is detected and measured by interferometry, said interferometric detection and measurement of the vertical displacement being carried out by measuring the vertical displacement of the structure surface before and immediately after the application of the thermal radiation pulse, said measurement giving a first signal indicative of the thermal expansion of the structure due to the amount of power absorbed by said structure, then measuring the vertical displacement during the inertial response of the structure after termination of the thermal radiation pulse, said other measurement giving another signal proportional to the vertical displacement of the coating; and using the first measured signal to normalize the second measured signal.

2. The improved method of claim 1, wherein the interferometric detection and measurement is carried out with a laser-beam interferometer.

3. The improved method of claim 2, wherein the pulsed, thermal radiations are generated by a laser beam.

4. The improved method of claim 2, wherein the laser-beam interferometer used for the detection and measurement of the vertical displacement of the coating is of the Michelson type.

5. The improved method of claim 2, wherein the laser-beam interferometer used for the detection and measurement of the vertical displacement of the coating is a laser-heterodyne interferometer.

6. The improved method of claim 5, comprising the steps of focusing the laser beam of the laser-heterodyne interferometer and using said focused laser beam as pulsed thermal radiations for heating the material.

7. In a device for detecting delaminated areas by thermal dilatometry in a layered structure comprising a substrate covered with a coating, said device comprising:

means for producing thermal radiations;

means for subjecting each surface area of the structure to said thermal radiations to produce a vertical displacement of its coating by thermal expansion wherever a delaminated area is present at the coating to-material interface; and means for detecting and measuring said vertical displacement, if any, the improvements wherein:

said means for producing thermal radiations comprises means for generating short pulses with a pulse duration that is ranging from 0.001 to 1 millisecond and is smaller than the mechanical response time of the delaminated area;

said means for subjecting the material to said radiations comprises means for focusing said radiations onto said structure to irradiate a surface area of said structure which is smaller than the smallest delaminated area which is to be detected; and said means for detecting and measuring said vertical displacement comprises an interferometer positioned to interferometrically compare the positions of the surface of the structure before and after each pulse in order to obtain a first signal indicative of the thermal expansion of the structure due to the amount of power absorbed by the structure, and a second signal indicative of the vertical displacement of the coating due to the inertial response of the structure after termination of the thermal radiation pulse, said first signal being used for normalizing the second signal.

8. The improved device of claim 8, wherein said interferometer is a laser-beam interferometer.

9. The improved device of claim 8, wherein said thermal radiation producing means is a laser beam.

10. The improved device of claim 9, wherein the laser-beam interferometer used for the detection and measurement of the vertical displacement of the coating is a laser-heterodyne interferometer.

11. The improved device of claim 10, wherein said thermal radiation producing means is the laser beam of the laser-heterodyne interferometer.

12. The improved device of claim 8, wherein the laser-beam interferometer used for the detection and measurement of the vertical displacement of the coating is of the Michelson type.

13. A method for detecting delaminated areas in a layered structure comprising a substrate and at least one covering layer, and having a predetermined inertial response time, said predetermined inertial response time being the inertial response time of the smallest delaminated area to be detected in the layered structure, said method including:

subjecting each surface area of the structure to be tested to thermal radiation consisting of a short pulse having a pulse duration smaller than the predetermined inertial response time of the layered structure and in the range of 0.001 to 1 millisecond, and wherein the thermal radiation is focused onto the surface of said structure to irradiate a surface area which is smaller than the delaminated areas to be detected; and detecting vertical displacements of the structure surface by interferometry to indicate delaminations by;

measuring a first vertical displacement of the structure surface during the application of the thermal radiation pulse as a measure of the thermal expansion of the structure due to the energy absorbed by the structure, measuring a second vertical displacement of the structure surface during the mechanical response time of the structure following the termination of the thermal radiation pulse as a measure of the thermal deformation in the structure, and using the first measured vertical displacement to normalize the second measured vertical displacement to provide an indication of a delamination, wherein the first vertical displacement measurement is obtained by determining the difference between an interferometric reading taken before the radiation pulse and an interferometric reading taken immediately after the termination of the radiation pulse.

14. The method of claim 13, wherein the second vertical displacement measurement is obtained by determining the difference between an interferometric reading taken before the radiation pulse and an interferometric reading taken a predetermined period of time after the termination of the radiation pulse equivalent to the mechanical response time of the structure.

15. The method of claim 13, wherein the second vertical displacement measurement is obtained by determining the difference between an interferometric reading taken immediately after the applied radiation pulse and an interferometric reading taken a predetermined period of time after the termination of the radiation pulse equivalent to the mechanical response time of the structure.

16. A device for detecting delaminated areas in a layered structure comprising of a substrate and at least one covering layer, and having a predetermined inertial response time, said predetermined inertial response time being the inertial response time of the smallest delaminated area to be detected in the layered structure, said device comprising:

means for generating pulses of thermal radiation wherein each pulse has a duration smaller than the predetermined inertial response time of the layered structure and in the range of 0.001 to 1 millisecond;

means for applying each surface are of the structure a short pulse of the thermal radiation as a focused beam to irradiate an area smaller than the delaminated area to be detected; and interferometric means for detecting vertical displacements of the structure surface to indicate delaminations, said interferometric means comprising:

means for measuring a first vertical displacement of the irradiated structure during the application of the thermal radiation pulse as a measure of the thermal expansion of the structure due to the absorption of thermal energy, means for measuring a second vertical displacement of the irradiated structure surface during the mechanical response time of the structure following the termination of the thermal radiation pulse as a measure of the thermal deformation in the structure; and means for normalizing the second measured vertical displacement with the first measured vertical displacement to provide an indication of a delamination.

17. A device as claimed in claim 16, wherein said means for measuring the first vertical displacement comprises means for determining the difference between an interferometric reading taken before the radiation pulse and an interferometric reading taken immediately after the termination of the radiation pulse.

18. A device as claimed in claim 17, wherein said means for measuring the second vertical displacement measurement comprises means for determining the difference between an interferometric reading taken before the radiation pulse and an interferometric reading taken a predetermined period of time after the termination of the radiation pulse equivalent to the mechanical response time of the structure.

19. A device as claimed in claim 17, wherein said means for measuring the second vertical displacement measurement comprises means for determining the difference between an interferometric reading taken immediately after the applied radiation pulse and an interferometric reading taken a predetermined period of time after the termination of the radiation pulse equivalent to the mechanical response time of the structure.

* * * * *